United States Patent
Breuniger

(10) Patent No.: US 11,191,269 B2
(45) Date of Patent: Dec. 7, 2021

(54) USE OF AN ACYCLIC PICOLINAMIDE COMPOUND AS A FUNGICIDE FOR FUNGAL DISEASES ON TURFGRASSES

(71) Applicant: Dow AgroSciences LLC, Indianapolis, IN (US)

(72) Inventor: James M Breuniger, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 16/610,097

(22) PCT Filed: May 2, 2018

(86) PCT No.: PCT/US2018/030561
§ 371 (c)(1),
(2) Date: Nov. 1, 2019

(87) PCT Pub. No.: WO2018/204438
PCT Pub. Date: Nov. 8, 2018

(65) Prior Publication Data
US 2020/0077654 A1 Mar. 12, 2020

Related U.S. Application Data

(60) Provisional application No. 62/500,195, filed on May 2, 2017.

(51) Int. Cl.
*A01N 43/40* (2006.01)
(52) U.S. Cl.
CPC .................................... *A01N 43/40* (2013.01)
(58) Field of Classification Search
None
See application file for complete search history.

(56) References Cited

U.S. PATENT DOCUMENTS

| | | |
|---|---|---|
| 4,051,173 A | 9/1977 | Schacht |
| 4,588,735 A | 5/1986 | Spatz |
| 5,342,835 A | 8/1994 | Pepin et al. |
| 5,401,871 A | 3/1995 | Talley |
| 5,475,132 A | 12/1995 | Pepin et al. |
| 5,563,165 A | 10/1996 | Talley |
| 5,665,351 A | 9/1997 | Nair et al. |
| 5,760,068 A | 6/1998 | Talley et al. |
| 5,852,042 A | 12/1998 | Jakobi |
| 6,355,660 B1 | 3/2002 | Ricks |
| 6,410,572 B1 | 6/2002 | Schelberger |
| 6,436,421 B1 | 8/2002 | Schindler |
| 6,521,622 B1 | 2/2003 | Ricks |
| 6,706,740 B2 | 3/2004 | Ricks |
| 6,812,237 B2 | 11/2004 | Cowen et al. |
| 6,812,238 B1 | 11/2004 | Fukuda et al. |
| 6,861,390 B2 | 3/2005 | Meyer |
| 6,903,219 B2 | 6/2005 | Niyaz |
| 6,916,932 B2 | 7/2005 | Meyer |
| 6,927,225 B2 | 8/2005 | Ricks |
| 6,953,807 B2 | 10/2005 | Hutin et al. |
| 7,034,035 B2 | 4/2006 | Ricks |
| 7,183,278 B1 | 2/2007 | Imamura |
| 7,241,804 B1 | 7/2007 | Hockenberry |
| 7,250,389 B1 | 7/2007 | Sakanaka |
| RE39,991 E | 1/2008 | Ricks |
| 7,442,672 B2 | 12/2008 | Muller |
| 7,458,581 B1 | 12/2008 | Derrer |
| 7,560,565 B2 | 7/2009 | Bacque |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra |
| 8,349,877 B2 | 1/2013 | Brix |
| 8,415,274 B2 | 4/2013 | Wachendorff-Neumann |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Anonymous, Synergistic Fungicidal Composition of Heterocyclic Aromatic Amides and Triazoles, IP.com Journal, IP.com, Electronic Publication, West Henrietta, NY, US, Jul. 2004, 11 pages.
Backman, P., Fungicide Formulation: Relationship to Biological Activity, Ann. Rev. Phytopathol, 1978, 16, pp. 211-237.
BASF New Fungicide Xemium Got Full Approval in EU, Agronews, Jul. 18, 2012 [retrieved on Feb. 4, 2014]. Retrieved from the Internet: ,URL:http://news.agropages.com/News/NewsDetail-7386.htm, 1 page.

(Continued)

*Primary Examiner* — Samantha L Shterengarts

(57) ABSTRACT

The present disclosure is related to the field of agrochemicals, including compound I and its use to control fungal diseases on turfgrasses.

Compound I

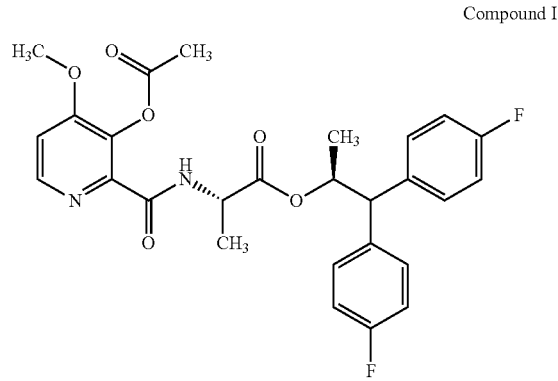

3 Claims, No Drawings

(56) References Cited

U.S. PATENT DOCUMENTS

| | | |
|---|---|---|
| 8,465,562 B2 | 6/2013 | Chen |
| 8,470,840 B2 | 6/2013 | Klittich |
| 8,476,193 B2 | 7/2013 | Keeney |
| 8,580,959 B2 | 11/2013 | Devasthale |
| 8,586,550 B2 | 11/2013 | Lee et al. |
| 8,604,215 B2 | 12/2013 | Phiasivongsa |
| 8,785,479 B2 | 7/2014 | Meyer |
| 8,835,462 B2 | 9/2014 | Meyer |
| 8,883,811 B2 | 11/2014 | Owen |
| 8,916,579 B2 | 12/2014 | Boebel |
| 9,006,259 B2 | 1/2015 | Boebel |
| 9,084,418 B2 | 7/2015 | Ehr |
| 9,131,690 B2 | 9/2015 | Meyer |
| 9,144,239 B2 | 9/2015 | Meyer |
| 9,155,305 B2 | 10/2015 | Gary |
| 9,156,816 B2 | 10/2015 | Ito |
| 9,179,674 B2 | 11/2015 | Martin |
| 9,185,911 B2 | 11/2015 | Inami |
| 9,198,419 B2 | 12/2015 | Owen |
| 9,247,741 B2 | 2/2016 | DeLorbe |
| 9,265,253 B2 | 2/2016 | Li |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin |
| 9,482,661 B2 | 11/2016 | Ross |
| 9,549,555 B2 | 1/2017 | DeLorbe |
| 9,549,556 B2 | 1/2017 | DeKorver |
| 9,629,365 B2 | 4/2017 | Li |
| 9,681,664 B2 | 6/2017 | Lalonde |
| 9,686,984 B2 | 6/2017 | DeKorver |
| 9,700,047 B2 | 7/2017 | Lu |
| 9,750,248 B2 | 9/2017 | Ouimette |
| 9,828,408 B2 | 11/2017 | Kalayanov et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 10,015,964 B2 | 7/2018 | Ogawa et al. |
| 10,015,966 B2 | 7/2018 | Taggi et al. |
| 2002/0119979 A1 | 8/2002 | Degenhardt |
| 2002/0177578 A1 | 11/2002 | Ricks |
| 2003/0018052 A1 | 1/2003 | Ricks |
| 2003/0022902 A1 | 1/2003 | Ricks |
| 2003/0022903 A1 | 1/2003 | Ricks |
| 2005/0239873 A1 | 10/2005 | Hockenberry |
| 2006/0167281 A1 | 7/2006 | Meijer |
| 2007/0010401 A1 | 1/2007 | Noon |
| 2007/0066629 A1 | 3/2007 | Tormo |
| 2009/0203770 A1 | 8/2009 | Hockenberry |
| 2009/0306142 A1 | 12/2009 | Carson |
| 2010/0016163 A1 | 1/2010 | Keiper |
| 2011/0070278 A1 | 3/2011 | Lopez |
| 2011/0082162 A1 | 4/2011 | Lorsbach |
| 2012/0245031 A1 | 9/2012 | Gewehr |
| 2013/0296372 A1 | 11/2013 | Owen |
| 2014/0051678 A1 | 2/2014 | Clement-Schatlo |
| 2014/0187587 A1 | 7/2014 | Ouimette et al. |
| 2014/0357713 A1 | 12/2014 | Damaj |
| 2015/0289508 A1 | 10/2015 | Meyer |
| 2015/0322051 A1 | 11/2015 | Lu |
| 2016/0037774 A1 | 2/2016 | Schulz |
| 2016/0183526 A1 | 6/2016 | Hopkins |
| 2016/0183527 A1 | 6/2016 | Hopkins |
| 2016/0330957 A1 | 11/2016 | Quiroz et al. |
| 2017/0183324 A1 | 6/2017 | Li |
| 2017/0360038 A1 | 6/2017 | Yao |
| 2017/0273303 A1 | 9/2017 | DeKorver |
| 2017/0273306 A1 | 9/2017 | Lalonde |
| 2017/0290333 A1 | 10/2017 | Bravo-Altamirano |
| 2017/0295792 A1 | 10/2017 | Bravo-Altamirano |
| 2017/0369421 A1 | 12/2017 | Yao |
| 2018/0000075 A1 | 1/2018 | Bravo-Altamirano et al. |
| 2018/0000080 A1 | 1/2018 | Buchan |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0037541 A1 | 2/2018 | Yao |

FOREIGN PATENT DOCUMENTS

| | | |
|---|---|---|
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 199741103 | 6/1997 |
| WO | 1997019908 | 6/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | 2012020777 | 8/2011 |
| WO | 2012016989 | 2/2012 |
| WO | 2016109301 | 12/2012 |
| WO | 2013136275 A1 | 9/2013 |
| WO | 2016007525 | 7/2015 |
| WO | 2016109288 | 12/2015 |
| WO | 2016109289 | 12/2015 |
| WO | 2016109290 | 12/2015 |
| WO | 2016109291 | 12/2015 |
| WO | 2016109300 | 12/2015 |
| WO | 2016109302 | 12/2015 |
| WO | 2016109303 | 12/2015 |
| WO | 2016109304 | 12/2015 |
| WO | 2016109305 | 12/2015 |
| WO | 2016106138 A1 | 6/2016 |
| WO | 2015005355 | 3/2017 |

OTHER PUBLICATIONS

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

Cantacuzene, D., "Optimization of the papain catalyzed esterification of amino acids by alcohols and diols," Tetrahedron 45, 3 (1989): 741-748.

FRAC Code List: Fungicides Sorted by Mode of Action (including FRAC Code numbering), Fungicide Resistance Action Committee, Dec. 2008, 10 pages.

Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.

Gisi, U., "Synergistic Interaction of Fungicides in Mixtures," The American Phytopathology Society, vol. 86, No. 11, 1996, pp. 1273-1279.

Guseynov et al: "Study of the reaction of aminoacetic acid with dihydric alcohols and production of epoxy esters" Chemical Problems, 2009 (1), pp. 188-190.

Hu, Z. et al., "Synthesis of Novel Analogues of Antimycin A3," Tetrahedron Letters 49 (2008), pp. 5192-5195.

Huang, C. et al., "Synergistic Interactions between Chitinase ChiCW and Fungicides Against Plant Fungal Pathogens," J. Microbiol. Biotechnol., 2008, 18(4), pp. 784-787.

Kissling, E., "Crop Protection Pipeline Value Jumps to Euro 2.4 Billion," BASF SE, Mar. 10, 2011 [retrieved on Feb. 4, 2014],

(56) References Cited

OTHER PUBLICATIONS

Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Jul. 2008, pp. 84-87.
Ueki, M., et al., "UK-2A, B, C, and D, Novel Antifungal Antibiotics from Streptomyces sp. 517-02 I. Fermentation, Isolation, and Biological Properties," The Journal of Antibiotics, vol. 49, No. 7, Jul. 1996, pp. 639-634.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 6 pages.
Tani, K. et al., "UK2A, B, C, and D, Novel Antifungal Antibiotics—from Streptomyces sp. 517-02.," The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from Streptomyces sp 517-02," Bioorganic & Medicinal Chemistry Letters, vol. 15, No. 8, 2005, pp. 2011-2014.
Usuki, Y. et al., "UK-2A, B, C, and D, Novel Antifungal Antibiotics from Streptomyces sp. 517-02 VI (2). Structure-activity Relationships of UK-2A," Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Goellner et al. "Phakopsora pachyrhizi, the causal agent of Asian soybean rust." Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, ACS Symposium Series Washington, D.C. vol. 606, pp. 13-34 (1995).

Patani et al. Bioisterism: A rational approach in drug design. Chemical Reviews, vol. 96, No. 8, pp. 3147-3176 (1996).
Kendall, S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total synthesis of the antifungal dilactones UK-2A and UK-3a: The determination of their relative and absolute configurations, analog synthesis and antifungal activities". Tetrahedron, vol. 54, pp. 12745-12774 (1998).
Lippard, S. "Chemical Synthesis: The Art of Chemistry". Nature, vol. 416, p. 587 (2002).
Washburn, W.N., "Identification of a nonbasic melanin hormone receptor 1 antagonist as an antiobesity clinical candidate." Journal of medicinal chemistry 57, 18 (Aug. 28, 2014): 7509-7522.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from Streptomyces sp 517-02 II. Structural Elucidation." The Journal of Antibiotics, vol. 49, Issue 12, pp. 1226-1231 (1996).
Shibata et al. "UK1, A Novel Cytotoxic Metabolite from Streptomyces sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Ueki, M., et al., "UK-1, A Novel Cytotoxic Metabolite from Streptomyces sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from Streptomyces sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from Streptomyces sp. 517-02". The Journal of Antibiotics, vol. 50, Issue 12, pp. 1052-1057 (1997).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.

USE OF AN ACYCLIC PICOLINAMIDE COMPOUND AS A FUNGICIDE FOR FUNGAL DISEASES ON TURFGRASSES

CROSS-REFERENCE TO RELATED APPLICATIONS

This is a national phase entry under 35 U.S.C. § 371 of international patent application PCT/US18/030561, filed on May 2, 2018 and published in English as international patent publication WO2018204438 on Nov. 8, 2018, which claims priority to the benefit of U.S. Provisional Patent Application Ser. No. 62/500,195 filed May 2, 2017, which is expressly incorporated by reference herein.

FIELD OF THE INVENTION

This present disclosure is related to the field of the use of (S)-1,1-bis(4-fluorophenyl)propan-2-yl (3-acetoxy-4-methoxypicolinoyl)-L-alaninate to control fungal diseases on turfgrasses.

BACKGROUND AND SUMMARY OF THE INVENTION

Fungicides are compounds, of natural or synthetic origin, which act to protect and cure plants against damage caused by agriculturally-relevant fungi. Generally, no single fungicide is useful in all situations. In certain cases, naturally occurring pathogens have developed resistance to several classes of fungicides. Consequently, research is ongoing to produce fungicides that may have alternative modes of action, better performance, are easier to use, and cost less.

The present disclosure relates to (S)-1,1-bis(4-fluorophenyl)propan-2-yl (3-acetoxy-4-methoxypicolinoyl)-L-alaninate (compound I) and its use as a fungicide. Compound I may offer protection against ascomycetes, basidiomycetes, deuteromycetes and oomycetes.

One embodiment of the present disclosure includes a method of controlling a pathogen-induced disease in a plant that is at risk of being diseased from the pathogen comprising contacting the plant or an area adjacent to the plant with a composition including compound I.

Another embodiment of the present disclosure is a use of compound I for protection of a plant against attack by a phytopathogenic organism or the treatment of a plant infested by a phytopathogenic organism, comprising the application of compound I, or a composition including compound I to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising compound I and a phytologically acceptable carrier material.

DETAILED DESCRIPTION OF THE INVENTION

One exemplary embodiment of the present disclosure includes mixture for controlling the growth of fungi, the mixture including compound I:

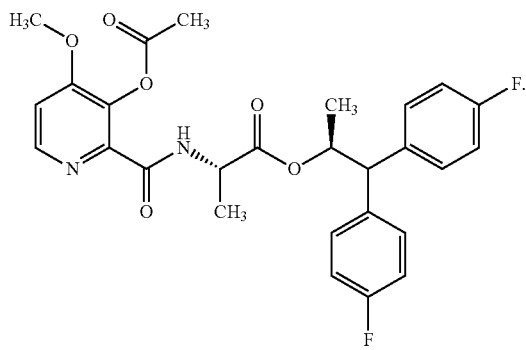

Compound I

Compound I of the present disclosure may be applied by any of a variety of known techniques, either as compound I or as formulations comprising compound I. For example, compound I may be applied to the roots, stems, seeds, flowers, or foliage of plants for the control of various fungi, without damaging the commercial value of the plants. Compound I may also be applied as a foliar spray, soil drench, soil injection, or seed treatment. The material may be applied in the form of any of the generally used formulation types, for example, as solutions, dusts, wettable powders, flowable concentrates, or emulsifiable concentrates.

Preferably, compound I of the present disclosure is applied in the form of a formulation, including compound I with a phytologically acceptable carrier. Concentrated formulations may be dispersed in water or other liquids for application, or formulations may be dust-like or granular, which may then be applied without further treatment. The formulations can be prepared according to procedures that are conventional in the agricultural chemical art.

The present disclosure contemplates all vehicles by which compound I may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which compound I may be added may be used, provided it yields the desired utility without significant interference with the activity of compound I as an antifungal agent.

Wettable powders, which may be compacted to form water-dispersible granules, comprise an intimate mixture including compound I, an inert carrier and surfactants. The concentration of compound I in the wettable powder may be from about 10 percent to about 90 percent by weight based on the total weight of the wettable powder, more preferably about 25 weight percent to about 75 weight percent. In the preparation of wettable powder formulations, compound I may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with compound I and milled.

Emulsifiable concentrates of compound I may comprise a convenient concentration, such as from about 10 weight percent to about 50 weight percent of compound I, in a suitable liquid, based on the total weight of the concentrate. Compound I may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum, such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of compound I of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with compound I. The formulations can also contain other compatible additives, for example, plant growth regulators and other biologically active compounds used in agriculture.

Aqueous suspensions including compound I may be dispersed in an aqueous vehicle at a concentration in the range from about 5 to about 50 weight percent, based on the total weight of the aqueous suspension. Suspensions are prepared by finely grinding compound I, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

Compound I may also be applied as a granular formulation, which is particularly useful for applications to the soil. Granular formulations generally contain from about 0.5 to about 10 weight percent (in this case it may go down as far as 0.10%), based on the total weight of the granular formulation of compound I, dispersed in an inert carrier which consists entirely or in large part of coarsely divided inert material such as attapulgite, bentonite, diatomite, clay, fertilizer, or a similar inexpensive substance. Such formulations are usually prepared by dissolving compound I in a suitable solvent and applying it to a granular carrier which has been preformed to the appropriate particle size, in the range of from about 0.5 to about 3 mm. A suitable solvent is a solvent in which compound I is substantially or completely soluble. Such formulations may also be prepared by making a dough or paste of the carrier and compound I and solvent, and crushing and drying to obtain the desired granular particle.

Dusts containing compound I may be prepared by intimately mixing compound I in powdered form with a suitable dusty agricultural carrier, such as, for example, kaolin clay, ground volcanic rock, and the like. Dusts can suitably contain from about 1 to about 10 weight percent of compound I, based on the total weight of the dust.

The formulations may additionally contain adjuvant surfactants to enhance deposition, wetting and penetration of compound I onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. Compound I and the pesticidal compound in the combination can generally be present in a weight ratio of from 1:100 to 100:1.

Compound I of the present disclosure may also be combined with other fungicides to form fungicidal mixtures and synergistic mixtures thereof. Compound I of the present disclosure is often applied in conjunction with one or more other fungicides to control a wider variety of undesirable diseases. When used in conjunction with other fungicide(s), the presently claimed compound I may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, aminopyrifen, ampropylfos, anilazine, azithiram, barium polysulfide, Bayer 32394, benodanil, benquinox, bentaluron, benzamacril; benzamacril-isobutyl, benzamorf, benzovindiflupyr, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, coumoxystrobin, cufraneb, cupric hydrazinium sulfate, cuprobam, cyclafuramid, cypendazole, cyprofuram, decafentin, dichlobentiazox, dichlone, dichlozoline, diclobutrazol, dimethirimol, dinocton, dinosulfon, dinoterbon, dipymetitrone, dipyrithione, ditalimfos, dodicin, drazoxolon, EBP, enoxastrobin, ESBP, etaconazole, etem, ethirim, fenaminosulf, fenaminstrobin, fenapanil, fenitropan, fenpicoxamid, fluindapyr, fluopimomide, fluotrimazole, flufenoxystrobin, furcarbanil, furconazole, furconazole-cis, furmecyclox, furophanate, glyodine, griseofulvin, halacrinate, Hercules 3944, hexylthiofos, ICIA0858, inpyrfluxam, ipfentrifluconazole, ipflufenoquin, isofetamid, isoflucypram, isopamphos, isovaledione, mandestrobin, mebenil, mecarbinzid, mefentrifluconazole, metazoxolon, methfuroxam, methylmercury dicyandiamide, metsulfovax, metyltetraprole, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, oxathiapiprolin, phenylmercury dimethyldithiocarbamate, phenylmercury nitrate, phosdiphen, picarbutrazox, prothiocarb; prothiocarb hydrochloride, pydiflumetofen, pyracarbolid, pyrapropoyne, pyraziflumid, pyridachlometyl, pyridinitril, pyrisoxazole, pyroxychlor, pyroxyfur, quinacetol, quinacetol sulfate, quinazamid, quinconazole, quinofumelin, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, triclopyricarb, triflumezopyrim, urbacid, zarilamid, and any combinations thereof.

Additionally, compound I of the present invention may be combined with other pesticides, including insecticides, nematicides, miticides, arthropodicides, bactericides or combinations thereof that are compatible with compound I of the present invention in the medium selected for application, and not antagonistic to the activity of compound I, to form pesticidal mixtures and synergistic mixtures thereof. Compound I of the present disclosure may be applied in conjunction with one or more other pesticides to control a wider variety of undesirable pests. When used in conjunction with other pesticides, the presently claimed compound I may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as broflanilide, chlorantraniliprole, cyantraniliprole, cyclaniliprole, cyhalodiamide, flubendiamide, tetrachlorantraniliprole, and tetraniliprole; diarylisoxazoline insecticides such as fluxametamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; mesoionic insecticides such as dicloromezotiaz and triflumezopyrim; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; pyridylpyrazole insecticides such as tyclopyrazoflor; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, cycloxaprid, imidacloprid, nitenpyram, and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, kappa-bifenthrin, bioethanomethrin, chloroprallethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, heptafluthrin, imiprothrin, meperfluthrin, metofluthrin, epsilon-metofluthrin, momfluorothrin, epsilon-momfluorothrin, permethrin, biopermethrin, transpermethrin, phenothrin, prallethrin, profluthrin, pyresmethrin, resmethrin, bioresmethrin, cismethrin, tefluthrin, kappa-tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spiropidion and spirotetramat; tetronic acid insecticides such as spiromesifen; thiourea insecticides such as diafenthiuron; urea insecticides such as flucofuron and sulcofuron; unclassified nematicides such as fluazaindolizine and tioxazafen; and unclassified insecticides such as benzpyrimoxan, closantel, copper naphthenate, crotamiton, EXD, fenazaflor, fenoxacrim, fluhexafon, flupyrimin, hydramethylnon, isoprothiolane, malonoben, metaflumizone, nifluridide, oxazolsulfyl, plifenate, pyridaben, pyridalyl, pyrifluquinazon, rafoxanide, sulfoxaflor, triarathene and triazamate, and any combinations thereof.

Additionally, compound I of the present invention may be combined with herbicides that are compatible with compound I of the present invention in the medium selected for application, and not antagonistic to the activity of compound I to form pesticidal mixtures and synergistic mixtures thereof. The fungicidal compound I of the present disclosure may be applied in conjunction with one or more herbicides to control a wide variety of undesirable plants. When used in conjunction with herbicides, the presently claimed compound I may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid, tebutam and tiafenacil; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid, florpyrauxifen, halauxifen, and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as fenquinotrione, lancotrione, mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmediphamethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, cyclopyranil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, tolpyralate, and topramezone; phenylpyrazole herbicides such as fluazolate, nipyraclofen, pioxaden and pyraflufen; pyridazine herbicides such as credazine, cyclopyrimorate, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, florpyrauxifen, fluroxypyr, halauxifen, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron, metribuzin, and trifludimoxazin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil, tiafenacil, and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, iofensulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, cyclopyrimorate, ortho-dichlorobenzene, dimepiperate, endothal, fluoromidine, fluridone, flurochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

Compound I of the present invention can also comprise or may be applied together and/or sequentially with further active compounds. These further compounds can be plant health stimulants, such as organic compounds, inorganic fertilizers, or micronutrient donors or other preparations that influence plant growth, such as inoculants.

In another embodiment, Compound I can also comprise or may be applied together and/or sequentially with other biological organisms, such as, but not limited to the group consisting of *Bacillus* strains, for example *Bacillus subtilis* var. *amyloiquefaciens* FZB24 (TAEGRP®) and *Bacillus amyloiquefaciens* FZB42 (RHIZOVITAL®), VotiVo™ *Bacillus firmus*, Clariva™ (*Pasteuria nishizawae*), *Bacillus thuringiensis, Trichoderma* spp., and/or mutants and metabolites of the respective strains that exhibit activity against insects, mites, nematodaes, and/or phytopathogens One embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidal effective amount of compound I. Compound I is suitable for treatment of various plants at fungicidal levels, while exhibiting low phytotoxicity. Compound I may be useful both in a protectant and/or an eradicant fashion.

The compound of Formula I has been found to have significant fungicidal effects particularly for agricultural use. The compound of Formula I is particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Turfgrass is known as a grass useful for covering a surface area of ground, typically subject to regular maintenance, such as golf courses and other commercial or residential turf areas such as athletic fields, lawns, municipal areas and cemeteries, or other ornamental turf areas. Turfgrass includes cool season turfgrass and warm season turfgrass.

Examples of cool season turfgrasses include, but are not limited to, Bluegrasses (*Poa* L.), such as Kentucky Bluegrass (*Poa pratensis* L.), Rough Bluegrass (*Poa trivialis* L.), Canada Bluegrass (*Poa compressa* L.), and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.), and Redtop (*Agrostis alba* L.); Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia* L.), Tall Fescue (*Festuca arundinacea* Schreb.), and Meadow Fescue (*Festuca elation* L.); Ryegrasses (*Lolium* L.), such as Perennial Ryegrass (*Lolium perenne* L.), and Annual (Italian) Ryegrass (*Lolium multiflorum* Lam.); Wheatgrasses (*Agropyron* Gaerin.), such as Fairway Wheatgrass (*Agropyron cristatum* (L.) Gaertn.), and Western Wheatgrass (*Agropyron smithii* Rydb.). Other cool season turfgrasses include Smooth Brome (*Bromus inermis* Leyss.) and Timothy (*Phleum* L.).

Examples of warm season turfgrasses include, but are not limited to, Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (Eremochloa ophiuroides (Munro.) Hack.), Carpetgrass (*Axonopus* Beauv.), Bahiagrass (*Paspalum notatum* Flugge.), Kikuyugrass (*Pennisetum clandestinum* Hochst. Ex Chiov.), Buffalograss (*Buchloe dactyloides* (Nutt.) Engelm.) and Seashore *paspalum* (*Paspalum vaginatum swartz*).

In particular, the composition is effective in controlling a variety of undesirable fungi that infect both warm season and cool season turfgrasses. The composition maybe used against a variety of *Ascomycete* and *Basidiomycete* fungi, including, for example, the following representative fungi species: Anthracnose (*Glomerella graminicola, Colletotrichum graminicola*), Ascochyta leaf blight (*Ascochyta* spp.), Brown and Large patch (*Rhizoctonia solani*), Brown ring patch (*Waitea circinata*), Copper spot (*Gloeocercospora sorghi*), Dead spot (*Ophiosphaerella agrostis*), Dollar spot (*Sclerotinia homoeocarpa*), Fairy ring (*Agaricus* spp., *Lepiota* spp., *Marasmius oreades, Lycoperdon* spp., *Agrocybe pediades*, etc.), Gray leaf spot (*Pyricularia grisea*), Gray snow mold (*Typhula* spp.), Leaf spot and Melting out (*Drechslera* spp., *Bipolaris* spp.), Leaf and sheath spot (*Waitea circinata* var. *zeae, Waitea circinata* var. *oryzae*), Necrotic ring spot (*Ophiosphaerella* spp.), Pink patch (*Limonomyces roseipellis*), Pink snow mold (*Microdochium nivale*), Powdery mildew (*Blumeria graminis*), *Pythium* blight (*Pythium* spp.), Red leaf spot (*Drechslera* (*Pyrenophora*) *erythrospila*). Red thread (*Laetisaria fuciformis*), Rust diseases (*Puccinia* spp.), Smut diseases (*Ustilago* spp.), Spring dead spot (*Ophiosphaerella korrae, O. herpotrich, O. narmari*), Summer patch (*Magnaporthe poae*), Take-all patch (*Gaeumannomyces graminis*), Yellow patch (*Rhizoctonia cerealis*), and Yellow tuft (*Sclerophthora macrospora*).

Compound I has been found to have significant fungicidal effects on phytopathogenic fungi of turfgrass. These diseases include *Sclerotinia homoeocarpa*, which causes dollar spot of turfgrass; and *Glomerella graminicola* or *Colletotrichum graminicola* which causes anthracnose of turfgrass, particularly for golf course, commercial and residential use. Compound I is particularly effective for use with agricultural crops and horticultural plants.

Compound I has a broad range of efficacy as a fungicide. The exact amount of the active material to be applied is dependent not only on the specific active material being applied, but also on the particular action desired, the fungal species to be controlled, and the stage of growth thereof, as well as the part of the plant or other product to be contacted with the compound. Thus, compound I, and formulations containing the same, may not be equally effective at similar concentrations or against the same fungal species.

Compound I is effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

EXAMPLES

Compound I

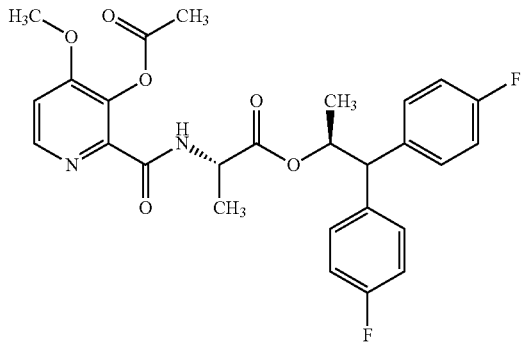

Field Assessment of *Sclerotinia homoeocarpa* (SCLEHO) on Creeping Bentgrass:

A fungicidal treatment containing Compound I, applied in a 10% suspension concentrate (SC) formulation and tank mixed with an adjuvant (Agnique BP420, 50% weight per weight (w/w) at 0.3% volume per volume (v/v)), was sprayed on a sward of creeping bentgrass (*Agrostis palustris* Huds.), maintained at a height of 0.45 centimeters (cm), at rates of 250 and 500 grams of active ingredient per hectare (g ai/ha). Irrigation and aerification operations were done according to standard practices for creeping bentgrass putting greens. The treatment was part of an experimental trial designed as a randomized complete block with four replications and a plot of approximately 1×6.6 meters (m). Dollar spot disease was allowed to develop from natural inoculum as the site was thoroughly involved in dollar spot and anthracnose symptoms in years past. Formulations of Compound I were applied using a custom-built boom sprayer. Three Tee-Jet air induction nozzles (AI9503EVS for the middle, AIUB8503EVS for both sides) were mounted approximately 30.4 cm apart on the boom located 35.5 cm from the ground. The sprayer was calibrated to deliver 804 liters per hectare (L/ha). Commercially available fungicides Eagle 20EW and Xzemplar Fungicide were used as commercial standards and were applied at label rates for dollar spot control. All treatments were applied three times at approximately 14-day intervals during the growing season of creeping bentgrass. The temperature levels were considered normal and ample precipitation and heavy dews promoted dollar spot establishment early in untreated plots. The environmental component of disease pressure was considered moderately high throughout the experimental period.

The progression of dollar spot infection (% visual disease severity) was recorded as the percentage of the plot infested with the disease. Experimental plots were assessed for disease six times during the trial at approximately 7-10 day intervals (8-41 days after application A, DAAA). The data in Table 1 show that formulations of Compound I significantly reduce dollar spot disease during the observation period and provided better control than Eagle 20EW and was equivalent to Xzemplar Fungicide when Compound I was applied at 500 g ai/ha.

Field Assessment of *Glomerella graminicola* (COLLGR) on Annual Bluegrass:

A fungicidal treatment containing Compound I, applied in both a 10% emulsifiable concentrate (EC) and 10% SC formulation and tank mixed with an adjuvant (Agnique BP420, 50% w/w at 0.3% v/v), was sprayed on a sward of annual bluegrass (*Poa annua*), maintained at a height of 0.45 cm, at rates of 250 and 500 grams of active ingredient per hectare (g ai/ha). Irrigation and aerification operations were done according to standard practices for *Poa annua* putting greens. The treatment was part of an experimental trial designed as a randomized complete block with four replications and a plot of approximately 1×6.6 m. Anthracnose disease was allowed to develop from natural inoculum as the site was thoroughly involved in dollar spot and anthracnose symptoms in years past. Formulations of Compound I were applied using a custom-built boom sprayer. Three Tee-Jet air induction nozzles (AI9503EVS for the middle, AIUB8503EVS for both sides) were mounted approximately 30.4 cm apart on the boom located 35.5 cm from the ground. The sprayer was calibrated to deliver 804 L/ha. The commercially available fungicide Velista was used as the commercial standard and was applied at label rates for anthracnose control. All treatments were applied three times at approximately 14 day intervals during the growing season of annual bluegrass. The first application (application A) was sprayed as a 10% EC formulation. The second and third treatments (application B and C) were applied as a 10% SC formulation. The temperature levels were considered normal and ample precipitation and heavy dews promoted anthracnose establishment early in untreated plots. The environmental component of disease pressure was considered moderately high throughout the experimental period.

The progression of anthracnose infection (% visual disease severity) was recorded as the percentage of the plot infested with the disease. Experimental plots were assessed for disease six times during the trial at approximately 7-10 day intervals (8-45 days after application A, DAAA). The data in Table 2 show that formulations of Compound I provided significant control of anthracnose disease of *Poa annua* putting greens with the 250 and 500 g ai/ha treatments being equivalent to the control provided by Velista.

TABLE 1

Efficacy of Compound I against Dollar Spot (*Sclerotinia homoeocarpa*, SCLEHO) on Creeping Bentgrass - Based on Percentage of the Plot Infested After Each Application

| | | Dollar Spot Infestation (% Visual) | | | | | | |
|---|---|---|---|---|---|---|---|---|
| Treatment | Rate* | 0 DAAA | 8 DAAA | 14 DAAA | 8 DAAB | 13 DAAB | 6 DAAC | 13 DAAC |
| Compound I | 250 | 2.2 | 0.8 | 0.7 | 0.8 | 1.1 | 0.6 | 2.1 |
| Compound I | 500 | 1.7 | 0.5 | 0.5 | 0.5 | 0.6 | 0.3 | 0.5 |
| Eagle 20EW | 306 | 1.7 | 0.8 | 2 | 2.9 | 3.5 | 2.4 | 15 |

TABLE 1-continued

Efficacy of Compound I against Dollar Spot (*Sclerotinia homoeocarpa*, SCLEHO) on Creeping Bentgrass - Based on Percentage of the Plot Infested After Each Application

| | | Dollar Spot Infestation (% Visual) | | | | | | |
|---|---|---|---|---|---|---|---|---|
| Treatment | Rate* | 0 DAAA | 8 DAAA | 14 DAAA | 8 DAAB | 13 DAAB | 6 DAAC | 13 DAAC |
| Xzemplar | 151 | 1.7 | 0.5 | 0.2 | 0.2 | 0.2 | 0.3 | 0.2 |
| Untreated | | 2.8 | 2.8 | 4 | 5.7 | 5.7 | 11.8 | 24.4 |

*Grams of active ingredient per hectare (g ai/ha)

TABLE 2

Efficacy of Compound I against Anthracnose (*Glomerella graminicola*, COLLGR) on *Poa Annua* - Based on Percentage of the Plot Infested After Each Application

| | | Anthracnose Infestation (% Visual) | | | | | | |
|---|---|---|---|---|---|---|---|---|
| Treatment | Rate* | 0 DAAA | 8 DAAA | 14 DAAA | 10 DAAB | 17 DAAB | 11 DAAC | 17 DAAC |
| Compound I | 250 | 22.1 | 7 | 7 | 22.1 | 11.5 | 11.5 | 22.1 |
| Compound I | 500 | 43.2 | 9.2 | 7 | 9.2 | 11.5 | 11.5 | 11.5 |
| Velista | 763 | 22.1 | 7 | 9.2 | 22.1 | 11.5 | 22.1 | 22.1 |
| Untreated | | 43.2 | 43.2 | 53.7 | 53.7 | 53.7 | 53.7 | 53.7 |

*Grams of active ingredient per hectare (g ai/ha)

What is claimed is:

1. A method of controlling fungal diseases on turfgrasses that are at risk of being diseased comprising the steps of: contacting at least a portion of a plant and/or an area adjacent to a plant with a composition comprises compound I

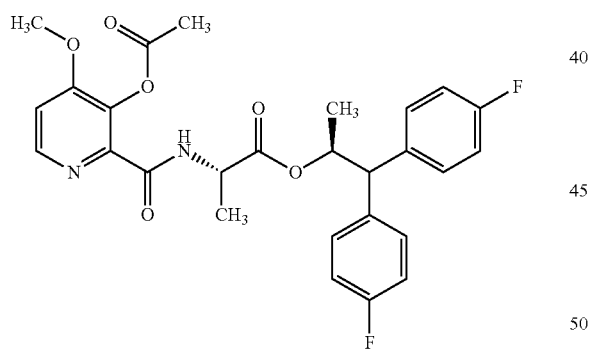

Compound I wherein said compound is effective against a fungal pathogen.

2. The method of claim 1, wherein the composition further includes at least one of one additional agriculturally active ingredient selected from the group consisting of: an insecticide, an herbicide, and a fungicide.

3. The method of claim 1, wherein the fungal pathogen is selected from the group consisting of the causal agents of: dollar spot on turfgrasses and anthracnose on turfgrasses.

* * * * *